United States Patent
Sheldon et al.

(10) Patent No.: US 10,437,960 B2
(45) Date of Patent: Oct. 8, 2019

(54) HEALTHCARE FACILITY MANAGEMENT AND INFORMATION SYSTEM

(71) Applicant: Scan Am Company, Algonquin, IL (US)

(72) Inventors: Daniel Sheldon, Barrington Hills, IL (US); Sonne DeVries, Barrington Hills, IL (US); Clare Cooke, Orland Park, IL (US); Dennis Bednar, Huntley, IL (US); William Bock, Mt. Prospect, IL (US); Randall Karlsen, McHenry, IL (US); Noel Wolbing, Lake In the Hills, IL (US); Saad Yusuf, Downers Grove, IL (US)

(73) Assignee: SHELDON INVESTMENT GROUP, INC., Algonquin, IL (US)

( * ) Notice: Subject to any disclaimer, the term of this patent is extended or adjusted under 35 U.S.C. 154(b) by 768 days.

(21) Appl. No.: 14/836,218

(22) Filed: Aug. 26, 2015

(65) Prior Publication Data

US 2015/0363556 A1    Dec. 17, 2015

Related U.S. Application Data

(62) Division of application No. 12/982,048, filed on Dec. 30, 2010, now abandoned.
(Continued)

(51) Int. Cl.
| | | |
|---|---|---|
| G06F 19/00 | (2018.01) | |
| G16H 40/20 | (2018.01) | |
| G16H 10/60 | (2018.01) | |

(Continued)

(52) U.S. Cl.
CPC ......... *G06F 19/3418* (2013.01); *G06Q 50/22* (2013.01); *G06Q 50/24* (2013.01); *G16H 10/60* (2018.01); *G16H 40/20* (2018.01)

(58) Field of Classification Search
CPC .... G06F 19/3418; G16H 40/20; G16H 10/60; G06Q 50/22; G06Q 50/24
See application file for complete search history.

(56) References Cited

U.S. PATENT DOCUMENTS

| | | |
|---|---|---|
| 7,475,019 B2 | 1/2009 | Rosenfeld et al. |
| 8,224,683 B2 | 7/2012 | Manos |

(Continued)

FOREIGN PATENT DOCUMENTS

| | | |
|---|---|---|
| EP | 2093724 A2 | 8/2009 |
| WO | WO 2010/052624 A1 | 5/2010 |

OTHER PUBLICATIONS

International Search Report from corresponding International Patent Application No. PCT/US2011/065040, dated Jul. 9, 2012.
(Continued)

*Primary Examiner* — Eliza A Lam
(74) *Attorney, Agent, or Firm* — Miller, Matthias & Hull LLP

(57) ABSTRACT

A method, system, computer program product and apparatus related to managing and disseminating information in a health care facility is disclosed. The system may comprise a plurality of input devices, a processor connected to the input devices and a plurality of electronic output devices connected to the processor. The output devices may include a master patient information display, an electronic patient room information display, a master precaution display, a patient hourly rounding display and an individual room precaution display. The method may comprises receiving from at least one input device data associated with a plurality of patients, and displaying for each patient the information, based on the data received, that is associated with each patient, and then updating on each output device the information when it changes.

15 Claims, 7 Drawing Sheets

Related U.S. Application Data

(60) Provisional application No. 61/387,006, filed on Sep. 28, 2010.

(51) Int. Cl.
*G06Q 50/22* (2018.01)
*G06Q 50/24* (2012.01)

(56) References Cited

U.S. PATENT DOCUMENTS

| | | | | |
|---|---|---|---|---|
| 8,237,551 | B2* | 8/2012 | Sweeney | A61B 5/1113 |
| | | | | 340/286.07 |
| 8,779,924 | B2* | 7/2014 | Pesot | A61B 5/0006 |
| | | | | 340/573.1 |
| 2003/0093300 | A1 | 5/2003 | Denholm | |
| 2004/0262377 | A1 | 12/2004 | Matz | |
| 2006/0049936 | A1 | 3/2006 | Collins, Jr. et al. | |
| 2006/0217987 | A1* | 9/2006 | Sowada | G08C 17/02 |
| | | | | 704/275 |
| 2006/0267753 | A1* | 11/2006 | Hussey | A61B 5/117 |
| | | | | 340/505 |
| 2007/0194939 | A1 | 8/2007 | Alvarez et al. | |
| 2008/0106374 | A1* | 5/2008 | Sharbaugh | G16H 40/20 |
| | | | | 340/5.8 |
| 2008/0281637 | A1 | 11/2008 | Matz | |
| 2009/0102612 | A1* | 4/2009 | Dalbow | A61N 5/1048 |
| | | | | 340/10.4 |
| 2010/0223071 | A1 | 9/2010 | Kland et al. | |
| 2011/0208541 | A1* | 8/2011 | Wilson | A61G 7/018 |
| | | | | 705/3 |
| 2012/0078661 | A1 | 3/2012 | Sheldon et al. | |

OTHER PUBLICATIONS

Supplementary European Search Report from corresponding European Application No. 11853139.1. dated May 25, 2016.
Canadian Office Action related to Application No. 2818035, dated Aug. 11, 2017.

* cited by examiner

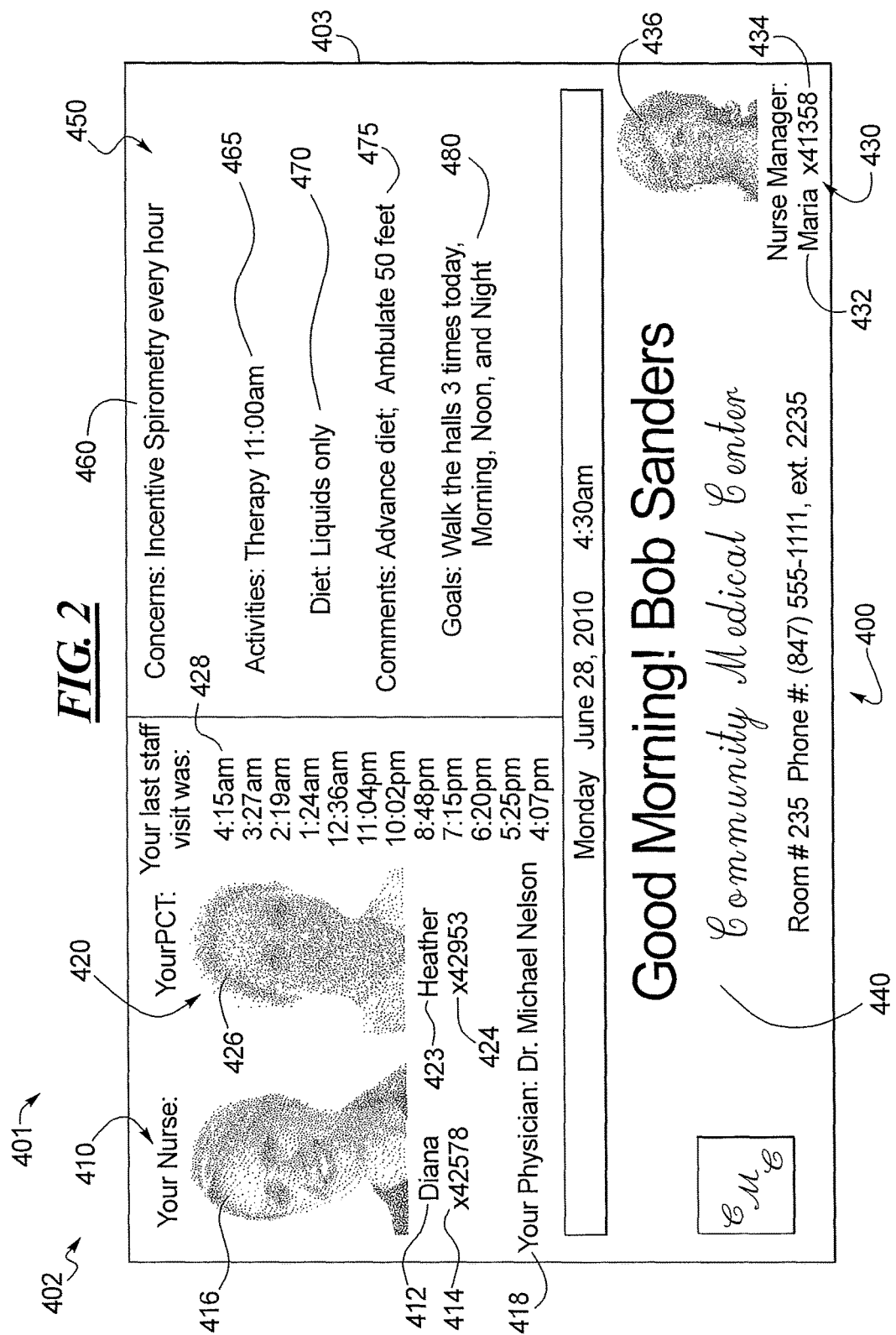

FIG. 3

Welcome to
*Community Medical Center*
Telemetry Unit

ROOM PRECAUTIONS — 510

| HR | Room | Patient | ISO | ACTVY | Fall | Allergy | Other |
|---|---|---|---|---|---|---|---|
| ○ | 201 | Stewart | | | | | |
| ○ | 202 | Riveria | | BR | FP | Sulfa | PUPP |
| HK | 203 | Ward | ISO | | | | |
| ○ | 204 | Peterson | VRE | | FP | | |
| ○ | 205 | Cox | TB/VRE | BRP | FP | | IV |
| ○ | 206 | Gray | ISO | BRP | FP | | IV |
| ○ | 207 | | | | | | |
| | 208 | Bennet | | BR | | | PUPP |
| ○ | 209 | Wood | NO | Wanders | FP | | |
| ○ | 210 | | | | | | |

ROOM PRECAUTIONS — 550

| HR | Room | Patient | ISO | ACTVY | Fall | Allergy | Other |
|---|---|---|---|---|---|---|---|
| ○ | 211 | Barnes | | | | Latex | ACCU |
| MRI | 212 | Foster | | BR | FP | PCN | PUPP |
| ○ | 213 | West | | BR | | | |
| ○ | 214 | Ellis | ISO | Assist | FP | | VENT |
| | 215 | Freeman | | | | | |
| MT | 216 | | | | | | |
| ○ | 217 | Olsen | | BRP | | | |
| ○ | 218 | Weaver | MRSA | UP | | | |
| ○ | 219 | Carr | | Assist | FP | Latex | |
| | 220 | | | | | | |

FIG. 5

Welcome to
*Community Medical Center*
Telemetry Unit

| HR | Status | Room | Patient | Nurse | PCT | RN Ext. | Admitting MD | Comments | ISO | ACTVY | Fall | Other |
|---|---|---|---|---|---|---|---|---|---|---|---|---|
| ○ | | 201 | Stewart | Rivers | Benson | 35426 | Santos | Social Service Consult | | | | |
| ○ | | 202 | Riveria | Keller | Benson | 35669 | Sutter | | | BR | FP | PUPP |
| ○ | Surg | 203 | Patel | Rivers | Benson | 35426 | Santos | OR Today | ISO | BRP | FP | IV |
| ○ | | 204 | Ellis | Keller | Arnold | 35669 | Vaneister | Lexington Hospital Today | ISO | Assist | FP | VENT |
| ○ | | 205 | Peterson | Welch | Reid | 35628 | Sutter | Up With 2 Person Assist | VRE | Assist | FP | |
| ○ | | 206 | Palon | Keller | Arnold | 35669 | Vaneister | VP | | UP | | |
| | HK | 207 | | | | | | | | | | |
| ○ | | 208 | Abusharif | Welch | Reid | 35628 | Thakkar | No English, No Female MDs | | BRP | | |
| ○ | | 209 | West | Rivers | Benson | 35426 | McGhee | Pending Discharge | | | | |
| ○ | | 210 | Wood | Rivers | Russel | 35426 | Gonzalez | Wanders: HX TIAS Dementia | NO | | FP | |
| ○ | | 211 | Barnes | Rivers | Benson | 35426 | Sutter | Diabetic | | | | ACCU |
| | | 212 | | | | | | | | | | |
| ○ | | 213 | Cox | Welch | Russel | 35628 | Santos | Pending Discharge W/Foley, Home Health F/U | TB/VRE | BRP | | IV |
| ○ | PT | 214 | Bennet | Keller | Arnold | 35669 | Narang | OT Eval, PT TID | | BR | | PUPP |
| ○ | | 215 | Freeman | Rivers | Russel | 35426 | Sutter | Discharge Today | | | | |
| ○ | | 216 | Miller | Rivers | Russel | 35426 | Sutter | Financial Consult/No Ins | ISO | BR | | PUPP |
| ○ | Card | 217 | Ward | Keller | Reid | 35669 | McGhee | NPO | ISO | | FP | |
| | MT | 218 | | | | | | Unavailable Until 8/10/2010 | | | | |
| ○ | | 219 | Weaver | Keller | Reid | 35669 | McGhee | Garden City Hospital - Admission Pending Ins. | MRSA | BRP | | |
| ○ | | 220 | Carr | Rivers | Reid | 35426 | Vaneister | Wanders | | Assist | FP | |

ROOM PRECAUTIONS

HOSPITAL NEWS:
Construction on new wing nearing completion,
please join us for the blessing this Sunday!

SHIFT NOTES:
Make a difference in someone's life today;
make our guest feel comfortable and rest well!

FIG. 6

Welcome to
*Community Medical Center*
Telemetry Unit

710

| Status | Room | Patient Name |
|---|---|---|
| ◯ | 201 | Stewart, Michael |
| ◯ | 202 | Riveria, Debbie |
| ◯ | 203 | Cox, Paul |
| ◯ | 204 | Ward, Greg |
| MRI | 205 | Peterson, Mark |
| ◯ | 206 | Gary, James |
| ◯ | 207 | Bennet, Marion |
| HK | 208 | Wood, Samantha |
| PT | 209 | Washington, Venessa |
| ◯ | 210 | Foster, Ken |
| ◯ | 201 | West, Vicky |
|  | 213 |  |
| SURG | 214 | Patel, Alkesh |

720

800

| Status | Room | Patient Name |
|---|---|---|
| ◯ | 215 | Hawkins, Melissa |
| ◯ | 216 | Synder, Steven |
| MT | 217 |  |
| ◯ | 218 | Olsen, Patty |
| ◯ | 219 | Weaver, Carolyn |
| ◯ | 220 | Armstrong, Todd |
| ◯ | 221 | Carr, Scott |
| ◯ | 223 | Rivers, Danielle |
| ◯ | 224 | Chapman, Russel |
| ◯ | 225 | Reid, Natile |
| ◯ | 226 | Welch, Karen |
| ◯ | 227 | Bowman, Ed |
| ◯ | 228 | Keller, Matt |
| ◯ | 229 | Benson, Roberta |

803

*CMC*

HEALTHCARE FACILITY MANAGEMENT AND INFORMATION SYSTEM

CROSS REFERENCE TO RELATED APPLICATION

This patent application is a divisional under 35 USC 121 of U.S. patent application Ser. No. 12/982,048 filed on Dec. 30, 2010, and claims the 35 USC § 119(e) benefit of U.S. Provisional Patent Application No. 61/387,006, filed on Sep. 28, 2010.

TECHNICAL FIELD

The present disclosure generally relates to computer based methods, systems and apparatus to provide information related to the status, condition or needs of a patient in a health care facility.

BACKGROUND

Patient satisfaction and patient-centered care go beyond patient needs and incorporate what patients and their families perceive as quality of care. Effective communication between patients, patient families, and nursing staff, as well as staff efficiency and accessibility, play key roles in determining how patients view their stay at a hospital, eldercare facility or other in-patient health care facility (collectively, "health care facilities"), and whether they will recommend your facility to their friends and loved ones. Poor communication or miscommunication, as well as lack of staff attention are highly detrimental to patients' perception of quality of care.

Traditional facility management and recordkeeping methods are a source of many health care delivery problems and staff and patient complaints. Many facilities still utilize some offline recordkeeping, often on an ad hoc basis due to the hectic nature of health care facilities. These poor management practices may also be reflected in unfavorable reviews and reports, such as Press Ganey™ facility reports.

From the patient perspective, a significant source of complaints relate to poor communication. For example, patients may complain that the patient and his loved ones are not kept appraised of past, present and future treatment plans. In addition to being poorly informed regarding the patient's health care, sometimes it is not clear to the patient who should be contacted for this information. While patients and family members may know the name of the patient's primary physician—who may or may not be present in the facility—they may not know the name and contact information for the nurses or patient care technicians (PCTs) who have current responsibility for the patient's care. In other cases, patients and family members may not be aware of the patient's dietary restrictions or special needs. Patients may not be aware of upcoming treatment and scheduled tests for a specific date. Some patients may even be confused about where they are and what day and time it is.

From the institution's perspective, it is desirable to reduce the amount of administrative time used to create staff schedules and patient care notices, such as precaution notices. In health care settings, such information is contained in the unit staff board, which includes information regarding nurse/patient room assignments and information regarding patients' illnesses as well as special instructions for individual patients. This information typically must be displayed in an area restricted to staff personnel to comply with HIPAA rules. This information may not only include health information but also financial resource information as well.

Some precaution notices are also displayed in patients' rooms and/or outside patients' rooms. In some facilities, these room precaution notices—notices posted for patients having special issues—may be paper and may be taped or pinned to a corkboard or written on a dry-erase board. Typical precautions relate to allergies, fall risk, and possible infections. Creating such notices on an ad hoc basis is time-consuming and if such notices are not noticeable and legible, they may be overlooked by the staff, creating potential treatment issues. Unusual or nonstandard precaution notices may result in confusion among staffers. Similarly, paper and whiteboard notices are also vulnerable to alteration. Further, if notices for a given patient change, these changes may be logged for future reference. Precautions could even remain up after the patient for whom they were intended has been transferred or discharged, resulting in inappropriate treatment.

Other administrative issues relate to internal institutional recordkeeping. One purpose of such recordkeeping is to ensure that individual staff members are not being overworked. Another purpose of such recordkeeping is to ensure that particular tasks are being performed on a timely basis, such as rotating sedentary patients to avoid decubitis ulcers, which can result in reductions in payments through Medicare and Medicaid. The process of staff members making periodic patient visits/rounds is generally known as Hourly Rounding. Health care facilities may not necessarily integrate records of their hourly rounds into their electronic records.

One measure of patient satisfaction relates to the promptness of the staff in responding to patient calls. The time between a patient call and staff response must be monitored to ensure quality care.

Many facilities participate in Press Ganey™ surveys of patients, staff and physicians regarding a facility's performance. Poor reports by patients could result in a reduction in patient admissions and have an adverse effect on the finances of the health care facility. There is a need to improved provision of information related to patients in health care facilities.

SUMMARY OF THE DISCLOSURE

In accordance with one aspect of the disclosure, a method of providing patient information is disclosed. The method may comprise receiving from at least one input device data associated with a first patient admitted to a health care facility, displaying patient information on an electronic room display disposed in the first patient's room in the health care facility, and updating the patient information on the room display when there is a change in the patient information. The patient information may include care provider information, treatment plan information and site information.

In accordance with another aspect of the disclosure, a computer program product is disclosed. The computer program product comprises a computer usable medium having a computer readable program code embodied therein. The computer readable program code may be adapted to be executed to implement a method for displaying patient information, the method comprising receiving from at least one input device data associated with a first patient admitted to a health care facility, displaying patient information on an electronic room display disposed in the first patient's room in the health care facility, the patient information including care provider information, treatment information and location information, and updating the patient information on the room display when there is a change in the patient information.

In accordance with a further aspect of the disclosure, a method of managing information in a health care facility is disclosed. The method may comprise providing a system including a plurality of input devices, a processor connected to the input devices and a plurality of electronic output devices connected to the processor, the output devices including an electronic patient room information display, a master precaution display, and an individual room precaution display; receiving from at least one of the input devices data related to a first patient admitted to the health care facility; associating the received data with the first patient; displaying patient information for the first patient on the electronic patient room information display; displaying on the master precaution display for a plurality of admitted patients precaution information and hourly rounding status information, the plurality of admitted patients including the first patient; and updating the patient information displayed on the electronic patient room information display when there is a change in the patient information for the first patient. In an embodiment, the patient room information display may be disposed in the first patient's room in the health care facility and the patient information may include care provider information, treatment plan information and site information.

In accordance with another aspect of the disclosure, a computer program product is disclosed. The computer program product may comprise a computer usable medium having a computer readable program code embodied therein. The computer readable program code may be adapted to be executed to implement a method for displaying information associated with a first patient. The method may comprise receiving from at least one of the input devices data related to a first patient admitted to the health care facility; associating the received data with the first patient and storing the associated data as information in a database; displaying at least some of the information associated with the first patient on an electronic patient room information display, a master precaution display, an individual room precaution display, a master patient information display and a patient hourly rounding display; and updating the displayed information when new data is received for the first patient.

In accordance with another aspect of the disclosure, an apparatus is disclosed comprising an electronic display device having a screen. The device may be configured to receive information associated with a patient admitted to a health care facility and to display the information on the screen. The device may be disposed in the room of a patient in a health care facility and the information displayed on the screen may comprise nurse assignment information, PCT assignment information, nurse manager information, physician information and a log of the most recent staff visits to the patient's room.

These and other aspects of this disclosure will become more readily apparent upon reading the following detailed description when taken in conjunction with the accompanying drawings.

BRIEF DESCRIPTION OF THE DRAWINGS

FIG. 2 is an exemplary screen shot according to one embodiment of patient information displayed on a patient room display.

FIG. 3 is an exemplary screen shot according to one embodiment of the master precaution display in accordance with the teachings of the disclosure.

FIG. 5 is an exemplary screen shot according to one embodiment of a patient information display in accordance with the teachings of the disclosure.

FIG. 6 is an exemplary screen shot according to one embodiment of a patient hourly rounding display in accordance with the teachings of the disclosure.

Figure 1:
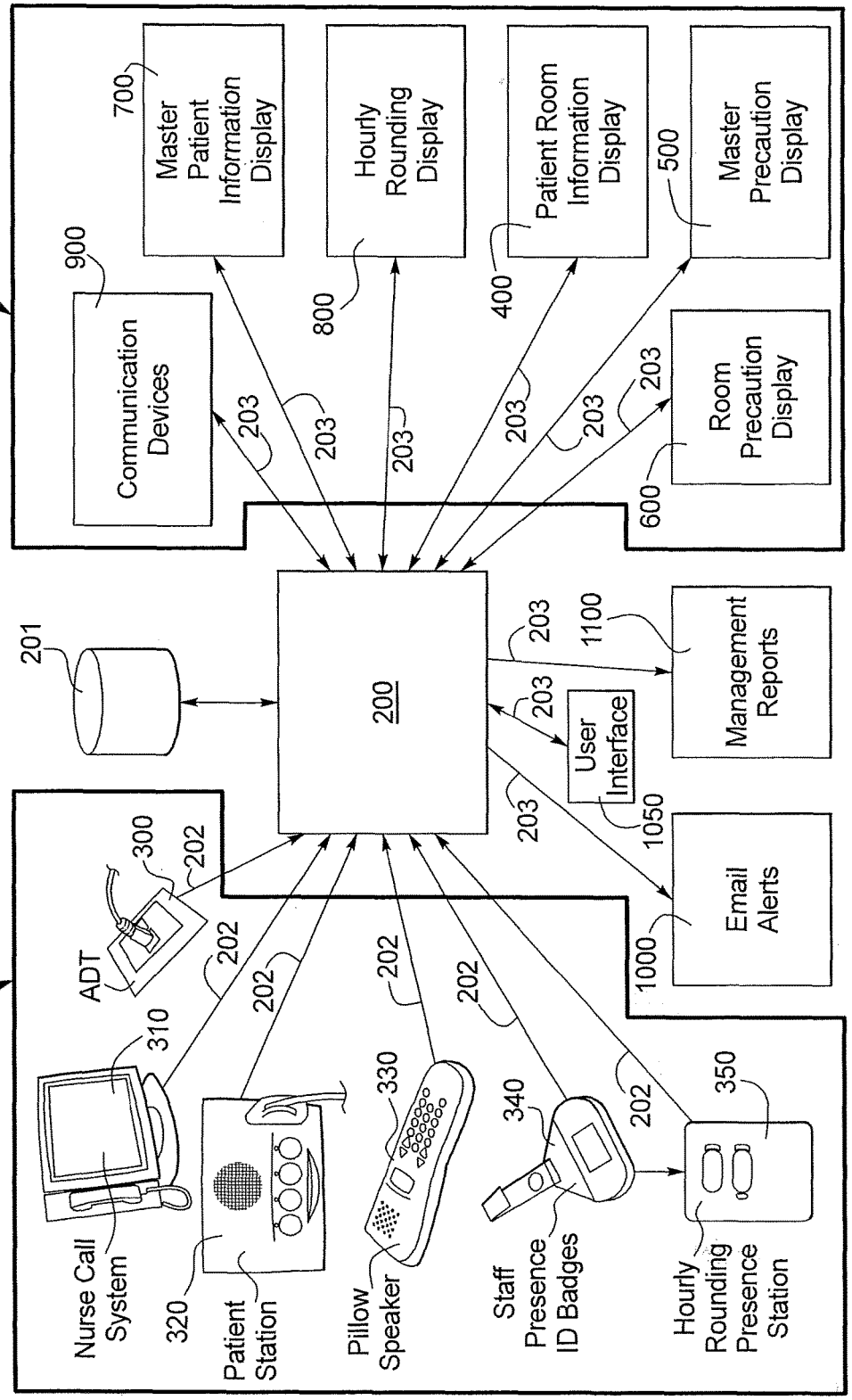
FIG. 1 is a schematic of one embodiment of a facility management system in accordance with the teachings of the disclosure.

While the present disclosure is susceptible to various modifications and alternative constructions, certain illustrative embodiments thereof have been shown in the drawings and will be described below in detail. It should be understood, however, that there is no intention to be limited to the specific forms disclosed, but on the contrary, the intention is to cover all modifications, alternative constructions, and equivalents falling within the spirit and scope of the present disclosure.

DETAILED DESCRIPTION

Turning to FIG. 1, the facility management system 100 may include at least one input device 208, a processor 200, a database 201 and at least one output device 209. Each input device may be connected to the processor by a communication link 202 and may transfer data to the processor 200 over the communication link 202. In an embodiment, a plurality of input devices 208 may be connected to the processor 200 by one or more communication links 202. The processor 200 may be connected to a database 201. At least one output device 209 may be connected to the processor 200 by a second communication link 203. Such an output device 209 may receive information from the processor 200. Some output devices 209 may transfer information to the processor 200 as well. Information received by the processor 200 from either an input device 208 or an output device 209 may be stored on the database 201. In some embodiments, a user interface 1050 may also be connected to the processor 200. In an embodiment, requests for reports and database 201 queries may be transmitted to the processor 200 through the user interface 1050.

The input device(s) 208 may comprise, but is/are not limited to: a facility's Admission/Discharge/Transfer (ADT) system 300, a nurse call system 310, a patient station 320, a patient room pillow speaker 330, a nurse presence ID badge 340, an hourly rounding presence station 350 and/or other devices that may be used to collect and/or store data collected from the patient, or his family, by the staff of the facility and to transfer such data collected to the processor 200.

The ADT system 300 may collect medical data/information regarding the patient as to their status (admitted, discharged or transferred). In an embodiment of the facility management system 100, when medical data is entered for a newly admitted patient in the ADT system, it is transferred to the processor 200 and may be available for display, as appropriate, on output devices 209 in the facility management system.

The nurse call station 310 may be used by nurses to enter data gathered during hourly rounds or other interaction with the patient.

The patient station 320 and pillow speaker 330 are devices that a patient may activate to summon facility staff members. When activated a signal may be sent over the communication link 202 to the processor 200. The processor 200 may update one or more output devices 209 to reflect the patient's request. The time between the patient's activation of a patient station 320 or a pillow speaker 330 and the response time of the staff may be logged by the processor 200. In one embodiment, the response time of the staff may be measured as the time between the activation of the patient station 320/pillow speaker 330 and the detection of a staff member's ID badge 340 by the rounding presence station 350 in the patient room. In an embodiment, the staff member's ID badge 340 may contain a tracking device, for example a RFID chip, that may be sensed by the rounding presence station 350 in the patient room. Once the staff member's ID badge 340 is sensed, a signal may be sent by the hourly rounding presence station 350 to the processor 200.

As noted above, the system 100 may include one or more output devices 209 whereby information generated by the system 100 may be displayed to facility staff and/or patients, as appropriate. These output devices 209 may include, but are not limited to, one or more of the following: a master patient information display 700, master precaution display 500, an individual room precaution display 600, a patient hourly rounding display 800, a patient room information display 400, and a staff communication device 900.

The data collected by the system 100 may be used by the processor 200 to populate output devices 209, such as master precaution display(s) 500, patient room information display(s) 400, master patient information display(s) 700 and patient hourly rounding display(s) 800, with information to be displayed throughout the facility, where appropriate. While in an embodiment these output devices 209 may be high definition flat screen apparatus, the output devices 209 are not limited to such apparatus. Output devices 209 may also display security screensavers to prevent unauthorized viewing of information.

Turning to FIG. 2, a patient room display 400 is shown. The patient room display 400 may be an electronic device having a screen 403 for outputting patient information 401 received from the processor 200. In an embodiment, the patient room display 400 may be a flat screen display and the relative position on the screen of the various components of patient information 401 may be customized based on the amount and type of patient information to be displayed, the dimensions of the screen 403 or even the arrangement of patient information desired. The patient room display 400 may be disposed in a patient's room. The patient may view the screen 403 on the patient room display 400 to see his/her patient information 401.

Patient information 401 may comprise care provider information 402, treatment plan information 450 and site information 440. In an embodiment, care provider information 402 may be displayed in a first area of the display and the treatment plan information may be displayed in a second area of the display. In other embodiments, other arrangements of the components of patient information 401 are possible.

In an embodiment, the care provider information 402 may include nurse assignment information 410, PCT assignment information 420, and nurse manager information 430. A PCT may be a facility staff member that is assigned to care for the patient. PCTs may include, but are not limited to, certified nursing assistants (CNAs), nurse's aides, and orderlies. In an embodiment, the care provider information may also include physician information 418. In yet another embodiment, the care provider information 402 may include staff visit information 428.

The nurse assignment information 410 may include the name of the nurse assigned to the patient (the "assigned nurse" name) 412, the assigned nurse's phone number 414 and an image of the assigned nurse 416.

The PCT assignment information 420 may include the name of at least one on-duty PCT that is assigned to the patient (the "assigned PCT name") 422, a phone number 424 and an image 426 of the on-duty assigned PCT.

The nurse manager information 430 may include the name of the supervisor or manager having supervisory responsibility for the nurse and the PCT assigned to the patient 432, the nurse manager's phone number 434 and his/her image 436.

The physician information 418 may include the name of the patient's physician and/or the name of the on-call physician.

The staff visit information 428 may comprise a listing of the most recent visit, or visits, to the patient's room by a nurse or other staff member of the facility, as logged by the processor 200. In one embodiment, the staff visit information 428 may include the time of the last twelve logged visits. In other embodiments the number of visits displayed may be greater or fewer than twelve, and both the time and date may be displayed.

The patient treatment plan information 450 may include, but is not limited to, patient health concern information 460 (for example, "latex allergy," or "sore throat" or "experiencing trouble swallowing"), patient planned activity information 465 (for example, "Therapy at 11:00 am"), patient current diet information 470 (for example, "liquids only"), staff treatment comments 475 (for example, "advance diet, ambulate 50 feet") and patient care goals 480 (for example, "walk the halls three times today, morning/noon/night").

The site information 440 may include the day of the week, the date, the time, message(s) from the facility to the patient, the name of the facility, and the patient's room and phone number.

FIG. 3 illustrates an exemplary embodiment of the master precaution display 500 on which precaution information 510 may be viewed on the screen 503 of the display 500. The master precaution display 500 may be located in a nurse station or other appropriate location in the facility. The precaution information 510 may include the name of each patient 512, the patient room number 514, isolation information 520 (for example, if there is concern regarding possible infections or communicable diseases), activity information 530 (such as a patient's tendency to wander), fall precaution information 540, patient allergy information 550, and other precaution information 560. The master precaution display 500 may also include hourly rounding status information 710 on the screen as well. The master precaution display 500 may be an electronic device having a screen for outputting precaution information 510 and/or hourly rounding status information 710 received from the processor 200. In an embodiment, the master precaution display 500 may be a flat screen display and the relative position on the screen of the various components of precaution information 510 and/or hourly rounding status information 710 may be customized based on the amount and type of precaution information 510 and/or hourly rounding status information 710 to be displayed, the dimensions of the screen 503 or even the arrangement of precaution information 510 and/or hourly rounding status information 710 desired.

Figure 4:
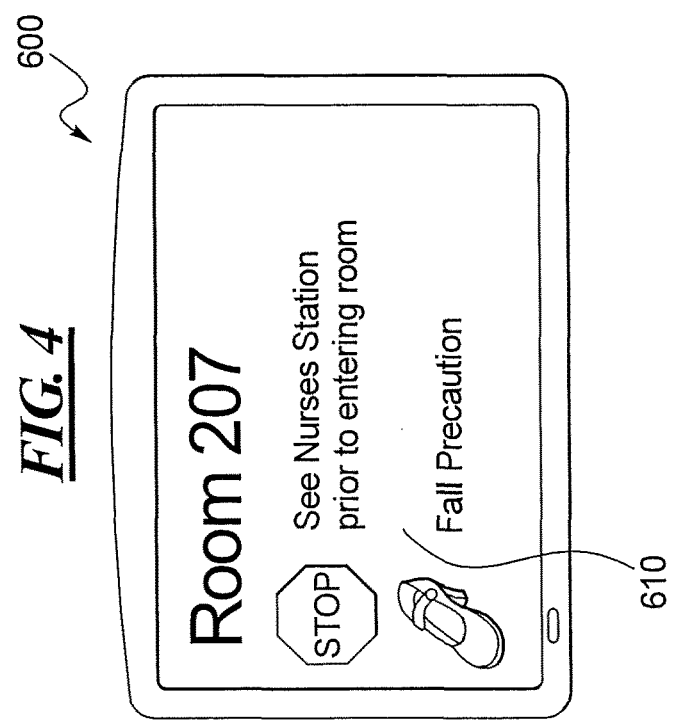
FIG. 4 is an exemplary screen shot according to one embodiment of a patient room precaution display in accordance with the teachings of the disclosure.

Turning now to FIG. 4, a patient room precaution display 600 is illustrated. The patient room precaution display 600 may be located outside each patient's room and may display a portion of the precaution information 510. If special precautions are to be taken with a particular patient, the patient room precaution display 600 may display a warning to advise a staff member or care provider to check the more detailed master precaution display 500 available at the nurse's station or other appropriate location.

Turning to FIG. 5, a master patient information display 700 having a screen 703 is shown. The master patient information display 700 may display information regarding each patient and, thus, may be placed in a location visible to only facility staff. The information that the master patient information display 700 provides on the screen 703 may include hourly rounding status information 710, patient location status information 720, patient room number 721, nurse assignment information 410, PCT assignment information 420, admitting physician information 730, staff comment information 740, and at some or all of the precaution information 510. Staff comment information 740 may include, for example, current treatment plans, the patient's financial status, and/or treatment to reflect the patient's personal or religious beliefs. In addition, the information shown on the master patient information display 700 may also comprise special announcements for staff including facility event information 750 and shift note information 760.

The master patient information display 700 may be an electronic device having a screen 703 for outputting information received from the processor 200 that is associated with patients that have been admitted to the facility. In an embodiment, the master patient information display 700 may be a flat screen display or an electronic whiteboard, and the amount and arrangement of the information displayed on the screen may be customized. Information for a plurality of patients may be displayed on the master patient information display 700, at the same time or on different pages or on different screens.

FIG. 6 shows a patient hourly rounding display 800 where the hourly rounding status 710 for each patient can be viewed. In an embodiment, for each room, the patient's name is displayed with hourly rounding status 710 for that patient. The patient hourly rounding display 800 may be an electronic device having a screen 803 for outputting information received from the processor 200 that is associated with patients that have been admitted to the facility. In an embodiment, the patient hourly rounding display 800 may be a flat screen display and the amount and arrangement of the information displayed on the screen 803 may be customized. Information for a plurality of patients may be displayed on the patient hourly rounding display 800, at the same time or on different pages shown on the screen.

Figure 7:
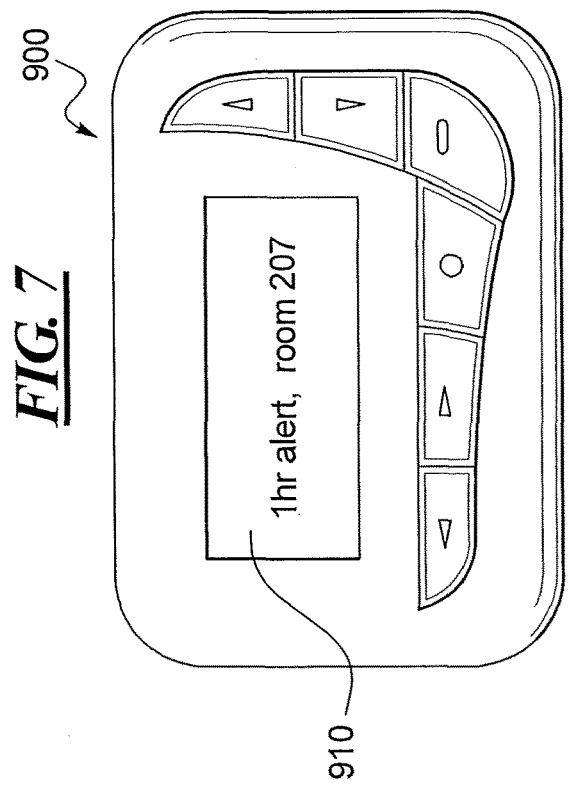
FIG. 7 is an exemplary embodiment of an alert displayed on one example of a staff communication device.

The hourly rounding status 710 may be a color coded flag that may change colors (or in some embodiments, shapes) to indicate the facility staff visit status for each patient. In one embodiment, the flag may be a circle and the circle may be green, yellow or red depending on how much time has passed since the last staff visit to the patient. For example, the flag may be red if more than an hour has passed since the last staff visit, the flag may be yellow if the time elapsed since the last staff visit is more than about fifty minutes and less than about one hour. Otherwise the flag may be green, signifying, in this embodiment, that the patient has been visited in the last fifty minutes by a member of the facility staff. In other embodiments, different shapes or icons may be used for the flag and different color coding may be used. If the patient is away from his room, the patient location status information 720 may be displayed in place of the rounding status, whereas, if the patient is present in the room, the hourly rounding status 710 may show that a visit to the room is necessary. In one embodiment of the system 100, if a staff visit is overdue an hourly rounding reminder 910 may be sent to the staff communications device 900, such as a pager or wireless phone or the like, as shown in FIG. 7. The hourly rounding reminder 910 may be text, an auditory alarm or message or a vibrating alarm.

The amount of time that elapses before the hourly rounding status 710 flag changes or before an hourly rounding reminder 910 is transmitted may be customized for all patients, a group of patients or for individual patients. The phrase "Hourly Rounding" or "hourly rounding" is not intended to be limited to periods of one hour but instead, as used herein, may cover time periods that may be longer or shorter than an hour. For example, a department manager in a facility, or other with appropriate authority, may set or change the frequency of the Hourly Rounding performed by facility staff to alternative time intervals other than one hour. At night, the frequency of such Hourly Rounding may be set for two hours, or another appropriate time interval. In addition, some patient's, because of care needs and the like, may need an Hourly Rounding frequency that is longer or shorter than other patients. The system 100 may accommodate such scenarios as above. For example, the time interval between when the hourly rounding status 710 changes from green to yellow may be longer or shorter than fifty minutes since the last staff visit and the time interval between when the hourly rounding status 710 changes from yellow to red (assuming no intervening staff visit) may be longer or shorter than ten minutes. In an embodiment, where the staff Hourly Rounding is set at nighttime to every two hours, the hourly rounding status 710 may be set to change for some or all of the patients from green to yellow when about one hour and fifty minutes have expired since the last staff visit and may be set to change to red when about two hours have expired since the last staff visit. There may be some patients for which two hour Hourly Rounding is not desirable. The Hourly Rounding for those individual patients may be customized. For example, in the scenario above, for certain individual patients, the hourly rounding status 710 may be set to change from green to yellow when about thirty-five minutes have expired since the last staff visit and may be set to change to red when about fifty minutes have expired since the last staff visit. The time intervals used in each scenario above are exemplary and other time intervals may be used in other embodiments.

When a staff member enters a patient's room, the hourly rounding presence station 350 may detect the presence of the staff member by the receipt of a signal that identifies the staff member. The received signal may be from an RFID tag disposed on the staff member (or in the staff ID badge 340), or a magnetic strip swiped through a card reader or a button or other device activated by a staff member to log their presence in the room. Upon receipt of a signal that identifies a staff member as having visited a patient's room, the hourly rounding presence station 350 may transmit that information to the processor 200. The processor may then store this information and use it to update information on the patient room display 400, the master precaution display 500, the master patient information display 700 and the patient hourly rounding display 800. For example, the hourly rounding status 710 may be updated from yellow (or red) to green to indicate that a staff member visited the patient, and the time of the visit may be displayed on the patient room information display 400.

The system 100 may generate reports 1100 regarding staff response times based on the stored time and date of the staff visit. These reports 1100 may comprise a comprehensive consulting and reports package for managing and improving response to nurse call light system activity. The reports 1100 generated may include reports by room, unit, department, floor, and facility-wide views of call light activity and the staff member's timeliness of response. Reports generated may present both detailed and summarized formats, plus exportable variations.

The system 100 may generate and output administrative reports 1100 to support managers in viewing department performance and working on follow-up. The system 100 may also output emails 1000 or text messages generated by processor 200. In an embodiment, the emails 1000 or text messages may include the reports 1100 as attachments or embedded in the email text, or may indicate that the reports 1100 are available.

In an embodiment, the processor 200 of the system 100 may centrally update and manage the output devices 209, whether the output device 209 is disposed in an individual patients' room or in a central location such as a nurse's station or doctor's lounge. For example, as shifts change, nurse assignment information 410, PCT assignment information 420, and nurse manager information 430 may be continuously updated along with the date and time information. Similarly, the patient room treatment plan information 450 may be updated with new test and treatment times or special notes, as added by doctors and facility staff, for the patient and family to view in the patient's room on the patient room display 400. Similarly, the master precaution display 500 may be updated to provide precaution information 510 from the processor 200. The master patient information display 700 may also be updated by the processor 200 to reflect changes in rounding status information 710 and patient location status information 720. For example if the patient is in a different part of the facility, this may be reflected in the patient location status information 720. Updating of information on the output displays 209 may be continuous or batched.

The locations and nature/type of output devices 209 included in the system 100 may be defined by rules applied by the processor 200 to the data received from the input devices 208 so that only information appropriate for the type of output device 209 and the location of the output device (public vs. private) is displayed. The system 100 may include a plurality of different types of output devices 209 having various screen sizes, deployed around the health care facility in a plurality of locations such as nurse stations, doctors' lounges, management offices, patient rooms and the like, (as appropriate, under privacy laws).

Figure 8:
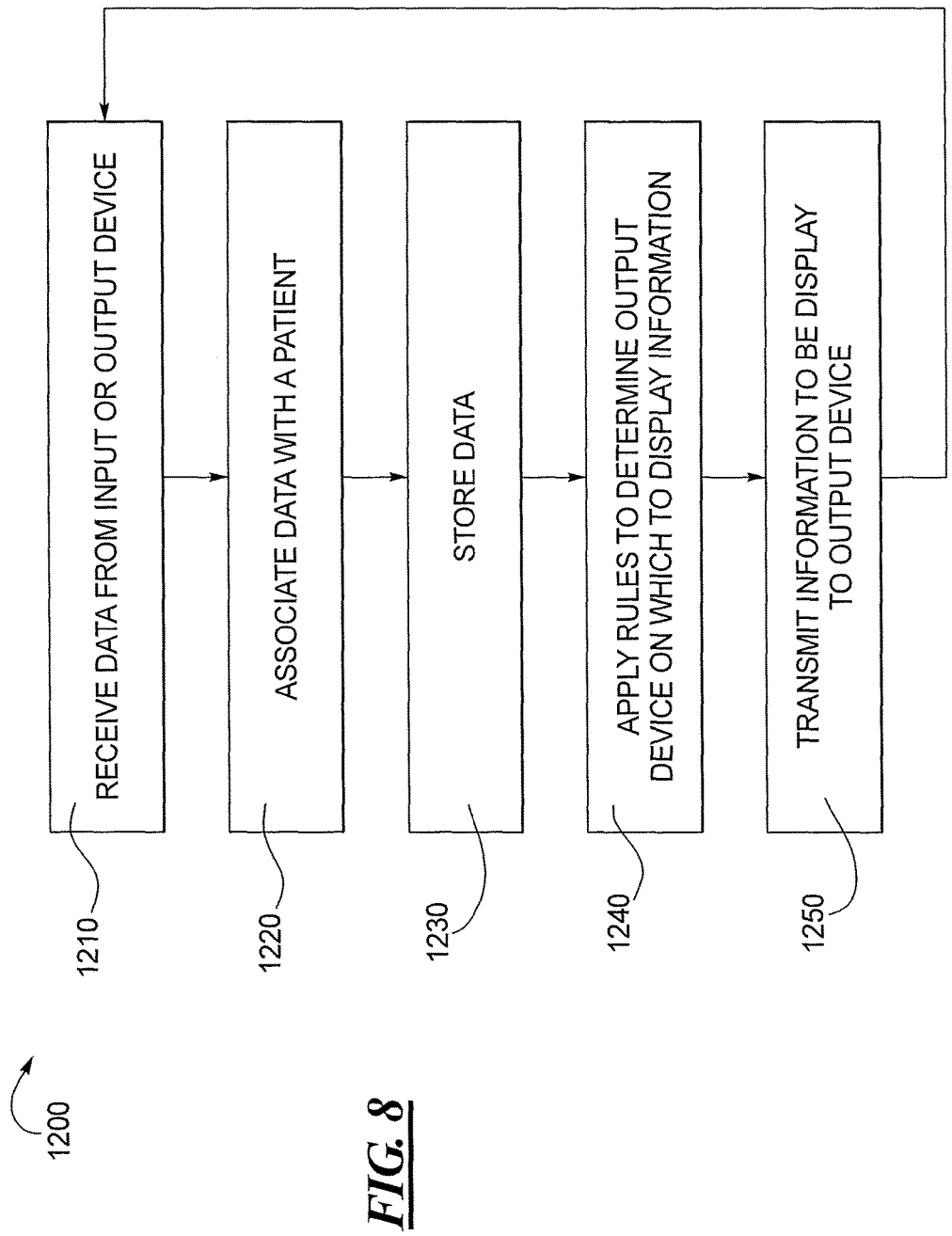
FIG. 8 is a flowchart depicting a sample sequence of steps which may be practiced according to a method of the present disclosure.

FIG. 8 is a flowchart 1200 depicting a sample sequence of steps which may be practiced according to a method of the present disclosure. As can be seen in step 1210, the processor 200 of the facility management system 100 receives input data from one or more input devices 208 over the communication link 202. In some scenarios, the processor 200 may also receive data from certain output devices 209 as well. In step 1220, the processor 200 executes computer readable program code to associate the data with a patient and formats the data. In step 1230, the processor 200 stores the data received from each input device 208 on the database 201. The data base 201 may store the data in a manner that maintains the association between the data received and the patient to whom it relates. In step 1240, rules defined in computer readable program code (embodied on a computer usable medium) adapted to be executed by the processor 200 may be applied to the received data to determine which output device(s) 209 should be populated, or updated, with some or all of the stored data. In step 1250, the processor 200 transmits across the second communication link 203 to each output device 209 information (representative of the data) to be displayed on the output device 209. As new data is received by the processor, the process is repeated.

The system 100 discussed herein makes reference to various elements such as a processor, a database, and a computer program product, and other computer-based devices (such as input and output devices), as well as actions taken and information sent to and from such elements. One of ordinary skill in the art will recognize the inherent flexibility of such a computer-based system that allows for a great variety of possible configurations, combinations, and divisions of tasks and functionality between and among component elements. For instance, methods and processes discussed herein may be implemented using a single computing device or multiple computing devices working in combination. Databases and applications may be implemented on a single system or may be in some embodiments distributed across multiple systems. Distributed components/elements may operate sequentially or in parallel. When data is obtained or accessed between a first and second computer system or component thereof, the actual data may travel between the systems directly or indirectly. For example, if a first computer accesses a file or data from a second computer, the access may involve one or more intermediary computers, proxies, and the like. The actual file or data may move between the computers, or one computer may provide a pointer or metafile that the second computer uses to access the actual data from a computer other than the first computer, for instance.

The present disclosure also makes reference to the relay of communicated data over communication links. It should be appreciated that such communication links may include, but are not limited to, a dial-in network, a local area network (LAN), wide area network (WAN), public switched telephone network (PSTN), the Internet, intranet or Ethernet type network and any other combination of hard-wired or wireless communication, for example, RF or cell-based communication links.

The disclosure contemplates methods, systems and computer program products on any machine readable media for accomplishing its operations. The various systems discussed herein are not limited to any particular hardware architecture or configuration. Embodiments may be implemented as a set of instructions residing on a computer-readable medium, such as a memory or hard disk, for execution on a general purpose computer or other processing device. Any suitable programming, scripting, or other type of language or combinations of languages may be used to implement the teachings contained herein. Such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor.

Suitable computing devices include multipurpose microprocessor-based computer systems accessing stored software, application-specific integrated circuits and other programmable logic, and combinations thereof.

While only certain embodiments have been set forth, alternatives and modifications will be apparent from the above description to those skilled in the art. These and other alternatives are considered equivalents and within the spirit and scope of this disclosure.

What is claimed is:

1. A healthcare facility management and information system, comprising:
   a computer processor provided within the healthcare facility and electronically coupled to a plurality of patient rooms and a central nurses station provided in the healthcare facility;
   a database in electronic communication with the processor;
   at least one of a pillow speaker and a patient station provided in each of the plurality of patient rooms and in electronic communication with the processor and central nurses station to enable a patient to call for a nurse;
   an electronic staff presence identification transceiver including a radio frequency identification tag worn by the nurse;
   an electronic rounding presence sensor positioned within each of the patient rooms and detecting the presence of the electronic staff presence identification transceiver worn by the nurse, the electronic rounding presence sensor being in electronic communication with the computer processor;
   an electronic patient information room display provided in each of the patient rooms and in communication with the healthcare facility computer processor, the electronic patient information display electronically displaying the name of the patient, the name of the nurse, the name of a physician responsible for the patient and at least the last ten times the nurse visited the patient room, the processor receiving signals from the electronic rounding presence sensor, tracking the last ten times the nurse visited the patient room, and calculating a time elapsed since the last rounding visit;
   an electronic hourly rounding display provided at the central nurses station, the electronic hourly rounding display electronically displaying the names of each patient in each of the plurality of patient rooms and a status icon representing the rounding status of each patient, the status icon being colored red if more than an hour has elapsed since the nurse has visited the patient, and rounding is due the icon being colored yellow if more than fifty minutes but less than an hour has passed since the nurse visited the patient, and the icon being colored green if the patient has been visited by the nurse in the preceding fifty minutes, the status icon changing color based on the time elapsed since the last rounding visit as calculated by the processor; and
   a plurality of wireless phones, each nurse having one of the plurality of wireless phones, each wireless phone receiving messages from the processor when patient rounding is due.

2. The healthcare facility management and information system of claim 1, further including a master patient information display provided at the central nurses station, the master patient information display being in electronic communication with the computer processor, the master patient information display electronically displaying all names of all patients, all nurses, all physicians, room numbers, round statuses, and room precautions.

3. The healthcare facility management and information system of claim 2, further including a plurality of room precautions displays, one of the room precaution displays being provided outside of each patient room, each room precaution display being in electronic communication with the computer processor, each room precaution display electronically displaying precautions to take with the patient with the patient room.

4. The healthcare facility management information system of claim 3, further including a master precaution display provided at the central nurses station, the master precautions display being in electronic communication with the computer processor, the master precautions display electronically displaying the names of all patients, the room numbers of all patients, the rounding status of all patients and the room precaution of all patients.

5. The healthcare facility management and information system of claim 4, wherein the plurality of room precaution displays electronically display messages informing nurses to check the master precautions display before entering the patient room.

6. The healthcare facility management and information system of claim 1, further including an admissions/discharge/transfer (ADT) station in electronic communication with the computer processor, the ADT station entering information about the patient at admission or discharge, the information being stored in the database by the processor.

7. A healthcare facility management and information system, comprising:
   a computer processor provided within the healthcare and electronically coupled to a plurality of patient rooms and a central nurses station in the healthcare facility;
   a database in electronic communication with the computer processor;
   a plurality of electronic staff presence identification transceivers worn by a plurality of nurses, each electronic staff presence identification transceiver including a radio frequency identification tag;
   an electronic rounding presence sensor positioned within each of the patient rooms and detecting the presence of the electronic staff presence identification transceivers worn by the plurality of nurses, the electronic rounding presence sensor being in electronic communication with the computer processor and automatically being informed of the exact time and nurse name upon entering the patient room, the processor receiving signals from the electronic rounding presence sensor, and calculating a time elapsed since the last rounding visit;
   an electronic hourly rounding display provided at the central nurses station, the electronic hourly rounding display being in electronic communication with the computer processor and electronically displaying the names of each of the plurality of patients in each of the plurality of patient rooms, and a status icon representing the rounding status of each patient, the status icon being colored a first color if rounding is overdue as determined by the processor, the status icon being colored a second color if rounding is due, the status icon being colored a third color if rounding is not due, the status icon changing color based on the time elapsed since the last rounding visit as calculated by the processor; and a plurality of wireless communication devices, one of the plurality of wireless communication devices being held by each of the plurality of nurses, each of the wireless communication devices receiving signals from the processor when the status icon changes color, each of the plurality of wireless communication devices displaying messages to the nurses that rounding is due or overdue.

8. The healthcare facility management and information system of claim 7, further including an electronic patient information room display provided in each of the patient rooms and in communication with the healthcare facility computer processor, the electronic patient room information display electronically displaying the name of the patient, the name of the nurse, the name of the physician responsible for the patient, and a rounding list providing a plurality of times the nurse has last visited the patient room.

9. The healthcare facility management and information system of claim 8, wherein the electronic patient information room display updates the rounding list automatically every time the nurse enters the patient room.

10. The healthcare facility management and information system of claim 9, further including an electronic master patient information display provided at the center nurses station, the master patient information display being in electronic communication with the healthcare facility computer processor, the master patient information display electronically displaying all the names of all patients, all nurses, all physicians, all room numbers, all rounding statuses and all room precautions.

11. The healthcare facility management and information system of claim 10, wherein the electronic master patient information display is automatically updated every time one of the nurses enters one of the patient rooms.

12. The healthcare facility management and information system of claim 11, further including at least one of a pillow speaker and a patient station provided in each of the plurality of patient rooms and in electronic communication with the processor and central nurses station to enable a patient to call a nurse.

13. The healthcare facility management and information system of claim 12, further including a plurality of room precautions displays, one of the room precaution displays being provided outside of each patient room, each room precaution display being in electronic communication with the computer processor, each room precaution display electronically displaying precautions to take with the patient with the patient room.

14. The healthcare facility management information system of claim 13, further including a master precaution display provided at the central nurses station, the master precautions display being in electronic communication with the computer processor, the master precautions display electronically displaying the names of all patients, the room numbers of all patients, the rounding status of all patients and the room precaution of all patients.

15. The healthcare facility management and information system of claim 14, wherein the plurality of room precaution displays electronically display messages informing nurses to check the master precautions display before entering the patient room.

\* \* \* \* \*